(12) United States Patent
Kennedy

(10) Patent No.: US 9,339,225 B2
(45) Date of Patent: May 17, 2016

(54) SYSTEMS AND METHODS FOR ASSESSING SWEAT GLAND OUTPUT

(71) Applicant: Daniel L. M. Kennedy, Minneapolis, MN (US)

(72) Inventor: William R. Kennedy, St. Paul, MN (US)

(73) Assignee: Daniel L. M Kennedy, Minneapolis, MN (US)

( * ) Notice: Subject to any disclaimer, the term of this patent is extended or adjusted under 35 U.S.C. 154(b) by 430 days.

(21) Appl. No.: 13/838,480

(22) Filed: Mar. 15, 2013

(65) Prior Publication Data

US 2014/0275862 A1 Sep. 18, 2014

(51) Int. Cl.
*A61B 5/00* (2006.01)

(52) U.S. Cl.
CPC ............ *A61B 5/4266* (2013.01); *A61B 5/0077* (2013.01)

(58) Field of Classification Search
CPC ........... A61B 5/14517; A61B 5/14521; A61B 5/4266
See application file for complete search history.

(56) References Cited

U.S. PATENT DOCUMENTS

| | | | |
|---|---|---|---|
| 3,753,099 A | 8/1973 | Kleinberg et al. | |
| 4,502,044 A * | 2/1985 | Farris ................ | G08B 21/20 340/604 |
| 2004/0136579 A1* | 7/2004 | Gutenev ........................ | 382/128 |
| 2008/0081964 A1* | 4/2008 | Zakrzewski ................. | 600/306 |
| 2010/0179403 A1* | 7/2010 | Martinsen et al. ............ | 600/346 |
| 2011/0152643 A1 | 6/2011 | Xue et al. | |
| 2012/0165626 A1* | 6/2012 | Irina et al. ...................... | 600/316 |
| 2013/0137991 A1* | 5/2013 | Fright et al. ................... | 600/476 |
| 2013/0245388 A1* | 9/2013 | Rafferty et al. ............... | 600/301 |
| 2015/0057515 A1* | 2/2015 | Hagen et al. .................. | 600/346 |

FOREIGN PATENT DOCUMENTS

WO WO-2013/152087 A2 * 10/2013 ............... B01L 3/00
WO WO-2014143733 A1 9/2014

OTHER PUBLICATIONS

Provitera et al. "Evaluation of sudomotor function in diabetes using the dynamic sweat test." Neurology. Jan. 5, 2010;74(1):50-6.*
Sato et al. "Regional and individual variations in the function of the human eccrine sweat gland." J Invest Dermatol. Jun. 1970;54(6):443-9.*
"International Application Serial No. PCT/US2014/027816, International Search Report mailed Jul. 11, 2014", 3 pgs.
"International Application Serial No. PCT/US2014/027816, Written Opinion mailed Jul. 11, 2014", 5 pgs.
Dulguerov, P., "Parotidectomy complications. New techniques for their objective evaluation, prevention and treatment", Ph.D. Thesis, Faculty of Medicine, University of Geneva, (1999), 7 pgs.

(Continued)

*Primary Examiner* — Navin Natnithithadha
*Assistant Examiner* — Meredith Weare
(74) *Attorney, Agent, or Firm* — Schwegman Lundberg & Woessner, P.A.

(57) ABSTRACT

Various method embodiments for performing a sweat test include triggering sweating in a test area of a test subject, drying the test area, and applying a test device on the test area. The test device is used to monitor sweat production of individual SGs within the test area to provide test results for each functional SG in the test area. The test results for each functional SG in the test area are recorded.

9 Claims, 18 Drawing Sheets

(56) References Cited

OTHER PUBLICATIONS

Gagnon, D., et al., "Modified iodine-paper technique for the standardized determination of sweat gland activation", J. Appl. Physiol., 112, (2012), 1419-1425.

Randall, W. C., "Quantitation and regional distribution of sweat glands in man", *J. Clin. Invest.*, 25(5), (Sep. 1946), 761-767.

Fealey, R. D., et al., "Thermoregulatory sweating abnormalities in diabetes mellitus", Mayo Clin. Proc., 64(6), (1989), 617-628.

Gibbons, C. H., et al., "QDIRT: quantitative direct and indirect test of sudomotor function", Neurology, 70(24), (2010), 2299-2304.

Gibbons, C. H., et al., "Quantification of sudomotor innervation: a comparison of three methods", Muscle Nerve, 42(1), (2010), 112-119.

Kennedy, W. R., "Collateral Reinnervation of Sweat Glands", Ann. Neurol., 15, Sakuta, (1984), 73-78.

Kennedy, W. R., et al., "Rodent Eccrine Sweat Glands: A Case of Multiple Efferent Innervation", Neuroscience, 11(3), (1984), 741-749.

Low, P. A., et al., "Quantitative sudomotor axon reflex test in normal and neuropathic subjects", Ann Neurol., 14(5), (Nov. 1983), 573-80.

Provitera, V., et al., "Evaluation of sudomotor function in diabetes using the dynamic sweat test", Neurology, 74(1), (2010), 50-56.

"International Application Serial No. PCT/US2014/027816, International Preliminary Report on Patentability mailed Sep. 24, 2015", 7 pgs.

* cited by examiner

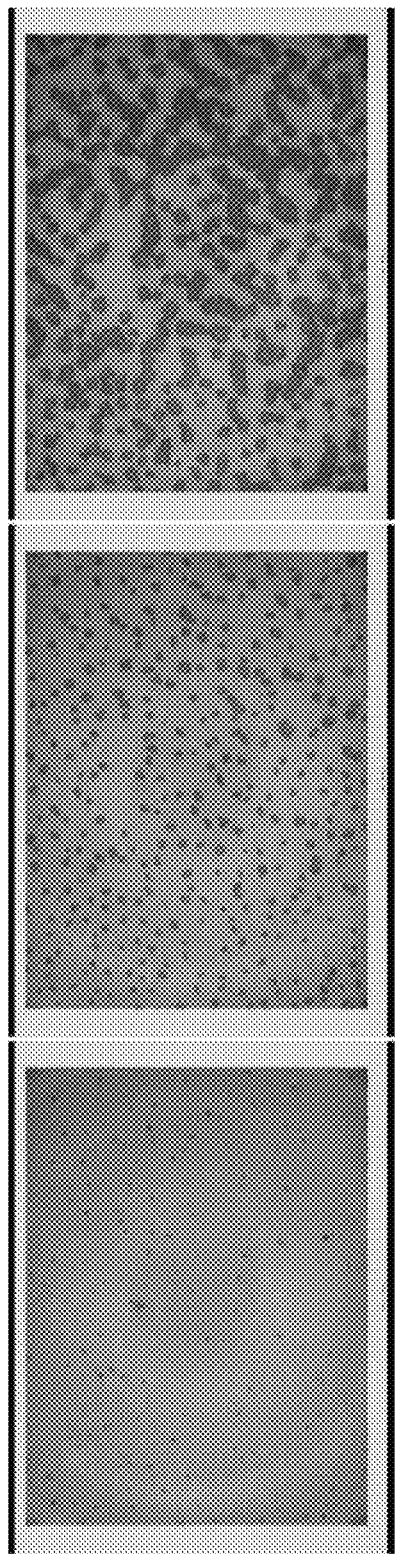

SYSTEMS AND METHODS FOR ASSESSING SWEAT GLAND OUTPUT

STATEMENT OF GOVERNMENT SUPPORT

This invention was made with government support under grant number NIH Grant 1R41NS078965-01, awarded by the National Institutes of Health. The U.S. government has certain rights in the invention.

TECHNICAL FIELD

This application relates generally to medical testing systems, devices and methods and, more particularly, to systems, devices and methods for assessing output from sweat glands (SGs).

BACKGROUND

Neuropathy is a diseased condition of the nervous system. There are many types of neuropathy. Some examples of neuropathy include, but are not limited to, diabetic neuropathy, chemotherapy-induced peripheral neuropathy (CIPN) human immunodeficiency virus (HIV), and alcoholic neuropathy.

SGs are activated by sudomotor nerves. Neuropathy often affects these sudomotor nerves. One way of analyzing a neuropathic condition of a patient is to evaluate the patient's ability to sweat. The following sweat tests for diagnosing neuropathy are known.

The quantitative sudomotor axon reflex test (QSART) is the most common test. It tests the volume of water produced by SGs in a 1-2 sq. cm area of skin (sweat water/area). Testing begins by iontophoresis of acetylcholine (ACh) into a ring of skin to stimulate SGs in the ring to sweat maximally. The sudomotor nerves (axons) innervating the SGs are also excited. These axons propagate the excitatory impulses proximally that reach the spinal level. However, excitation also flows peripherally at axon branch points toward the skin and excites SGs in other areas of the skin including an area in the center circle of the device (this is the reflex). Air is passed over this center circle to pick up the water that is measured over time. Water is produced only during iontophoresis due to the short survival of acetylcholine in the body. The QSART is mainly used in research studies, and is discussed in the following paper: Low P A, Caskey P E, Tuck R R, Fealey R D, Dyck P J, Quantitative sudomotor axon reflex test in normal and neuropathic subjects. Annals of Neurology. 1983; 14:573-580.

Another sweat test is the silastic mold test. This test was described in the Kennedy lab. The silastic mold test stimulates maximal sweating by iontophoresis of pilocarpine, and measures the number of activated SGs and their approximate secretion volume. The sweating skin is wiped dry and the area is then quickly covered with silastic material. Sweat secreted from SGs pushes into and leaves an impression in the still soft silastic material before the silastic material completely dries. The silastic material drying time may be about 4 minutes. The dried silastic mold can be viewed through a microscope at low magnification by shining light through the mold. The thinned areas that were indented by the sweat drops look like holes. These holes are easily counted. The diameter of the holes may be measured to calculate approximate volume. Thus, the silastic mold test may be used to provide a count of all active SGs in the area of skin tested and the approximate size of sweat droplets. The number of active SGs decreases as neuropathy progresses. The silastic mold test is discussed in the following paper: Kennedy W R, Sakuta M, Quick D C. Rodent eccrine sweat glands: a case of multiple efferent innervation. Neuroscience [0306-4522] Kennedy, W R yr:1984 vol:11 iss:3 pg:741-749.

Another sweat test is the thermoregulatory test, which shows body areas that do not sweat when the body is heated, presumably because the nerves to the SGs in those areas have degenerated. The patient is painted with a paste of starch and iodine and placed into a heated cabinet until the patient is sweating heavily. The paste on the patient becomes densely blue-black when in contact with sweat water. SGs in non-darkened skin are presumed to be unable to produce water because of nerve degeneration. The thermoregulatory test may be used to determine whether the patient is suffering from neuropathy and if so, where the neuropathy is located. The thermoregulatory test is discussed in the following paper: Fealey R D, Low P A, Thomas J E. Thermoregulatory sweating abnormalities in diabetes mellitus. *Mayo Clin Proc.* 1989 June; 64(6):617-28.

Another sweat test is the quantitative direct and indirect axon reflex testing (QDIRT) which evaluates sudomotor nerve function by measuring both the direct and axon-reflex mediated sweat response. SGs are stimulated by acetylcholine iontophoresis. A mixture of alizarin red, corn starch and sodium carbonate is quickly applied and digital photographs are taken $1/15$ sec. for 7 min. Sweat droplets are quantified by number, size and percent area over the area of interest, separating between direct and indirect sweat production. QDIRT is discussed in the following paper: Gibbons C H, Illigens B M, Centi J, Freeman R. QDIRT: quantitative direct and indirect test of sudomotor function. Neurology. 2008 Jun. 10; 70(24):2299-304. doi: 10.1212/01.wnl.0000314646.49565.c0. PMID: 18541883 [PubMed].

Another sweat test is the Dynamic Sweat Test (DST) developed by the Nolano lab in Italy and the Kennedy lab in Minnesota. The DST test may coat a sticky side of transparent tape with starch on the sticky side, and then place the tape onto the skin. The tape forces the sweat to spread laterally in a thin spot instead of a droplet. The edges of the dark spot are sharply imaged. The areas of the spots are measured at two times. The first time is just after tape is applied to the skin and the second time is when adjacent spots become confluent. If calibrated to known amounts of water, these two measurements can be used to manually calculate a change of a mean spot size over time (proportional to rate), mean sweat volume per $cm^2$ skin and volume per skin area stimulated. The DST has minimal to no evaporation of the sweat, and also provides maximal stimulation over 40 minutes by using pilocarpine to stimulate the sweat. DST is discussed in the following paper: Provitera V, Nolano M, Caporaso G, Stancanelli A, Santoro L, Kennedy W R. *Evaluation of sudomotor function in diabetes using the dynamic sweat test.* Neurology. 2010 Jan. 5; 74(1): 50-6. doi: 10.1212/WNL.0b013e3181c7da4b. PMID: 20038772

SUMMARY

Disclosed herein are systems, devices and methods for assessing output from sweat glands (SGs). Various embodiments measure features of sweating from a single SG to provide an objective and highly sensitive measure of sudomotor nerves that activate SGs. This measure of sudomotor nerves may be used to evaluate patients with neuropathy, including diabetic neuropathy, chemotherapy-induced peripheral neuropathy (CIPN) human immunodeficiency virus (HIV), alcoholic neuropathy and numerous other types of neuropathy.

Various method embodiments for performing a sweat test include triggering sweating in a test area of a test subject, drying the test area, and applying a test device on the test area. The test device is used to monitor sweat production of individual SGs within the test area to provide test results for each functional SG in the test area. The test results for each functional SG in the test area are recorded.

Various system embodiments for performing a sweat test on a test subject, include a test device and a processing system. The test device is configured to be applied to a test area on the test subject and to detect sweat production of individual SGs within the test area. The processing system is configured to analyze the detected sweat production, provide test results for each functional SG in the test area, and record the test results for each functional SG in the test area.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 4A, 4B, and 4C illustrate images taken early in the sweat test, in the middle of the sweat test, and late in the sweat test.

DETAILED DESCRIPTION

Figure 1:
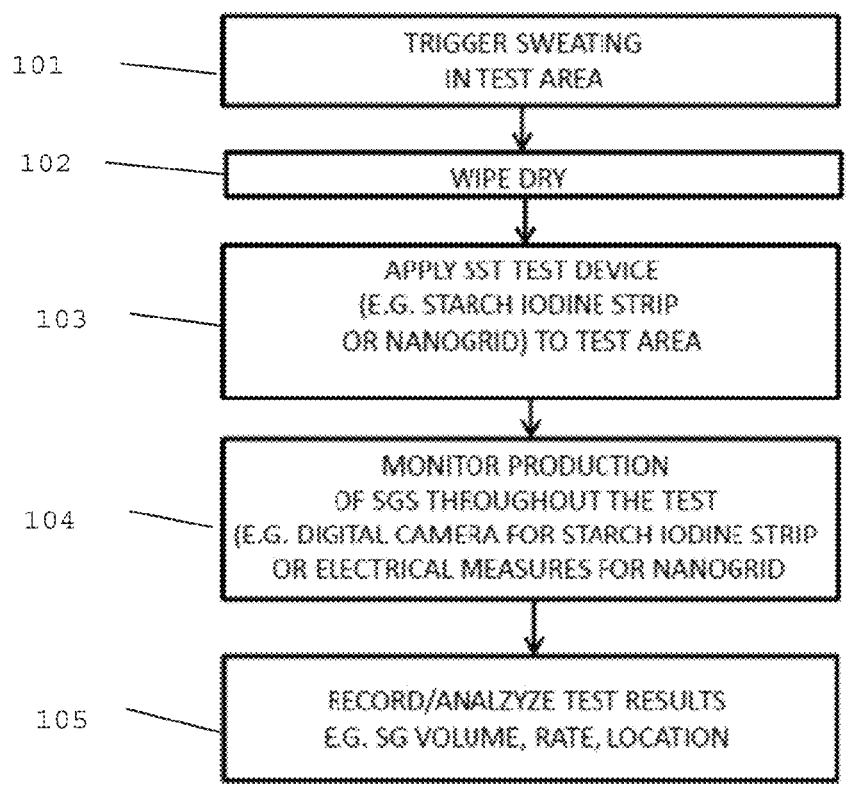
FIG. 1 illustrates an example of an SST flow diagram that may be used to evaluate peripheral neuropathy using a sweat test.

The following detailed description of the present subject matter refers to the accompanying drawings which show, by way of illustration, specific aspects and examples or embodiments in which the present subject matter may be practiced. These are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The diagnosis of neuropathy is usually made by detecting loss in one or more types of nerve activity, such as touch, pain, vibration, sweating or muscle function, or made by detecting abnormal nerve structure (pathology). If less sensitive tests are used, the neuropathy may progress and cause more nerve damage before detection. This delay in detection is undesirable because, as the damage to each nerve increases or as more nerves are damaged, it is less probable that the neuropathy can be halted or that the nerves can recover.

For example, cancer chemotherapy and diabetes are common causes of neuropathy in the USA. Both cause peripheral numbness, pain, decreased sweating, abnormal circulation, and eventually weakness. If diagnosed early, both are potentially treatable. In chemotherapy-induced neuropathy, chemicals used to treat cancer may not be tolerated by the patient. The patient may experience, for example, numbness and severe pain which are frequent causes of inadequate cancer treatment. A therapist has a better opportunity to adjust dosages, substitute chemical agents or add protective agents to moderate or stop neuropathy if it can be determined earlier that the patient has low tolerance of the chemicals used in the chemotherapy. Unfortunately, the minimal changes in function that first signal impending neuropathy escape detection by existing tests. Rather, existing tests detect changes in function after significant nerve degeneration. In elderly persons diabetic neuropathy usually develops before glucose levels reach the level accepted to diagnose diabetes. An early diagnosis of neuropathy can alert a patient and physician, allowing the patient an opportunity to address the condition through diet, exercise and other preventive measures to prevent diabetes and worsening of neuropathy.

The Sensitive Sweat Test (SST) is an objective, quantitative and highly-sensitive sweat test that may be used to diagnosis peripheral neuropathy early, when the probability for reversal is greatest. The SST device embodiments are convenient, affordable, and easily used in medical clinics, at the bedside or even in the home. SST is capable of reporting volume/area, but also capable of reporting the more detailed information about individual SG sweat rate and volume and information about active SG number and SG distribution. This sweat data for individual SGs is desirable, as it appears that each SG may have its own characteristic secretion rate. Furthermore, SGs recruit in a defined order, much like motor units. Dysfunction of secretion features, recruitment or features of sweat flow (smooth or pulsatile) at the level of the single SG is an early indicator of beginning neuropathy, and early detection of neuropathy provides better options for treating the neuropathy.

SST, as disclosed herein, addresses limitations of the QSART, silastic mold test, thermoregulatory test, QDIRT and DST. SST provides a more sensitive and accurate test required for early diagnosis and detection of the progress of neuropathies. SST is also easier to perform. In contrast, existing methods only recognize progression after gross changes of function over a prolonged time period causes patient symptoms. For example, QSART provides a sweat volume/area result, but does not provide data on sweat rate, individual SG rate, individual SG volume, SG number, or SG distribution. Furthermore, the instrument for perform QSART is expensive.

Although the silastic mold test provides a count of all active SGs in the area of skin tested and the approximate size of sweat droplets, there are many artifacts that resemble droplets and increase SG counts. Additionally, the total and individual SG volume is significantly underestimated because much of the sweat is secreted after the mold has hardened. Thus, these later secretions do not leave an impression in the mold and therefore are not recorded. Further, the silastic mold test does not provide dynamic data on SG rate.

The thermoregulatory test does not quantify sweat volume, SG number or SG distribution. Rather, the thermoregulatory test only shows the gross distribution of where sweating is not present.

Some limitations of QDIRT are that acetylcholine (unlike pilocarpine used in the SST) is rapidly destroyed in the body. As such, the full stimulation of SGs is short lived. Thus, some SGs may stop secreting sweat even before the imaging to obtain results begins. As such, the number of SGs is underestimated. For example, the estimated number of SGs using QDIRT may be half the number of SGs using the silastic method. Additionally, QDIRT has problems with estimating volume, because sweat evaporates with the exposure to air and this evaporation lowers estimated volume. Also, camera images of 3-D sweat droplets have indistinct margins. As a result, the estimated volumes of 3D sweat droplets can be inaccurate. QDIRT does not quantify the rate of secretion, volume of secretion per SG or SG size accurately.

DST also has limitations. For example, manual measurements were used to obtain sweat spot diameter at two times: after the tape is applied, and after adjacent spots become confluent. As the DST relies on these two manual measurements to obtain sweat spot diameter, the calculations are limited to mean rate and mean volume. The DST test cannot obtain individual SG rate or volume. Further, DST relies on commercial camcorder imaging at a distance, which is unsatisfactory for the required precision of the measurements to provide individual SG rate or volume. Additionally, the starch/tape strips are time consuming to make and are awkward to hold onto the camera, especially in clinic. The distribution pattern is analyzed by visual inspection only.

FIG. 1 illustrates an example of an SST flow diagram that may be used to evaluate peripheral neuropathy using a sweat test. At 101, significant sweating at a test area on the skin of the patient is triggered or induced. The induced sweat at the test area is wiped dry at 102, and an SST device is quickly applied to the test area 103 for use in monitoring the productions of the SGs throughout the test 104. As the SST is a sensitive test capable of analyzing the sweat production of each SG, test results such as, but not limited to, the sweat volume, rate and location of each SG may be recorded and analyzed 105. One embodiment of the SST uses starch tape and camera images to analyze the sweat production, and another embodiment of the SST uses a nano grid of nanoconductors to analyze the sweat production. These embodiments are described in detail below. The applied SST device 103 may be the starch tape, which also may be referred to as a starch iodine strip as a combination of starch and iodine are used by the digital camera to monitor sweat production 104. The applied SST device 103 may be a nano grid of nanoconductors that can be monitored at 104 to detect or measure electrical changes caused by sweat production.

Figure 2:
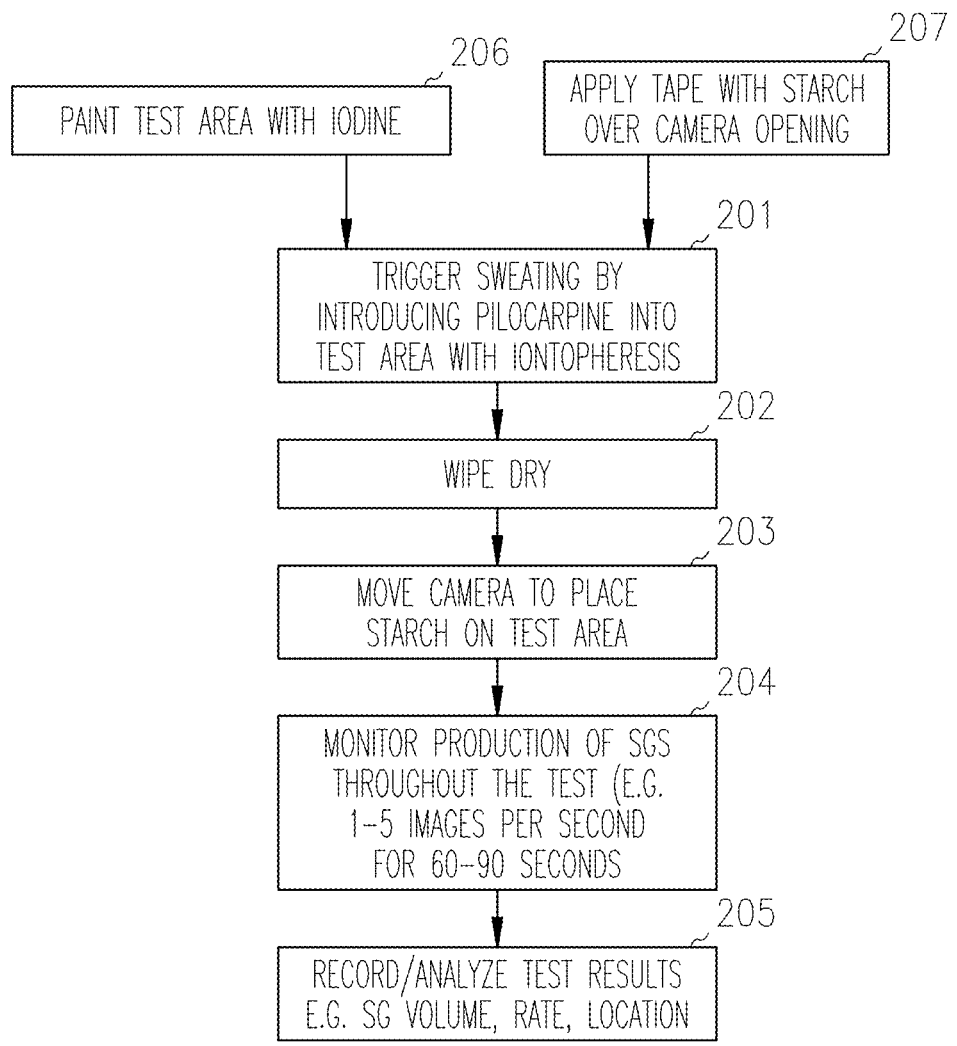
FIG. 2 illustrates an example of a starch tape embodiment that may be used to evaluate peripheral neuropathy during a sweat test.

FIG. 2 illustrates an example of a starch tape embodiment that may be used to evaluate peripheral neuropathy during a sweat test. As illustrated in the figure, preparations for making the sweat test measurements include painting the skin of the patient in the test area with iodine 206 and also include applying a transparent tape with starch on the tape over a camera opening 207. For example, a short strip of transparent tape, such as high quality packing tape, may be coated with a thin layer of starch such as corn starch. This tape will be attached over an opening of a small camera at a distance that allows the camera to focus on the starch. An iodine solution applied to the skin may be a 1% iodine solution. The iodine solution allows the starch to turn dark when in contact with sweat water. The dark spots produced at sweat duct openings provide good contrast and promote the precise imaging required to monitor and analyze the sweat production of each SG in the test area.

At 201, significant sweating at a test area on the skin of the patient is triggered or induced by introducing pilocarpine into the test area with iontophoresis. Pilocarpine may be used to stimulate SGs in the dermis of the skin to cause maximal sweating. For example, the SGs may be stimulated to secrete sweat by introducing 1% pilocarpine into the skin dermis within an approximately 2 $cm^2$ area using iontophoresis. The 2 $cm^2$ area contains approximately 200 sweat pores, depending on skin location. Iontophoresis uses electric current to deliver the pilocarpine into the skin. A simple stimulator may be used to apply the iontophoresis. For example, an approximately 2 milliamp direct current may be delivered to the area for approximately 5 minutes. More sophisticated stimulators may be used, such as a dual stimulator that simultaneously stimulates more than one skin area, measures time of current flow and has safety features that prevent excessive current. A small free standing, battery-powered unit may be designed for greater convenience and motility. The patch between the anode stimulator pad holder and skin may contain a buffer, $KNO_3$ or $KSO_4$, and pilocarpine. The ionophoresis may shift the pH and undesirably reduce the ability of the pilocarpine to be introduced in to the skin. The buffer reduces the problems with pH changes. The cathode pad may contain only $KNO_3$ or $KSO_4$ in solution or in a gel.

After a short interval (often 10 minutes) after iontophoresis to assure the desired SG secretion, the iodine painted skin is quickly wiped dry with a swift motion 202 and the camera is immediately pressed against the skin 203. As sweat water begins to exit from each of the sweat pores within the tested area, the sweat water contacts the starch/iodine and forms a tiny dark spot that begins to expand due to the force of continuous sweating. Pressure by the tape prevents formation of a sweat drop. Instead, sweat is forced to flow centrifugally, moving radially away from the sweat pore, between the tape and the skin to form a thin enlarging dark spot. Images of these dark spots may be used to analyze the sweat production. The camera takes a series of images over a period of time to monitor the sweat produced by the SG. For example, the images may be periodically taken one or more times per second, and may continue until adjacent spots coalesce. By way of example, and not limitation, the number of images taken may range from 1-5 images per second for a duration of 60 to 90 seconds. The image rate may be higher to provide more information about incremental changes in the image of the spot for recognition and calculation of sweat flow characteristics, or may be less to provide less information about incremental changes. The results of this test may be recorded and analyzed, as generally illustrated at 205. The imaging of these expanding black spots may be performed by a special short focal length miniature camera and wide angle lens. The camera may have a custom housing that contains field illuminating LEDs, signaling LEDs to indicate computer connectivity and ON/OFF imaging, molded diffusers.

Figure 3:
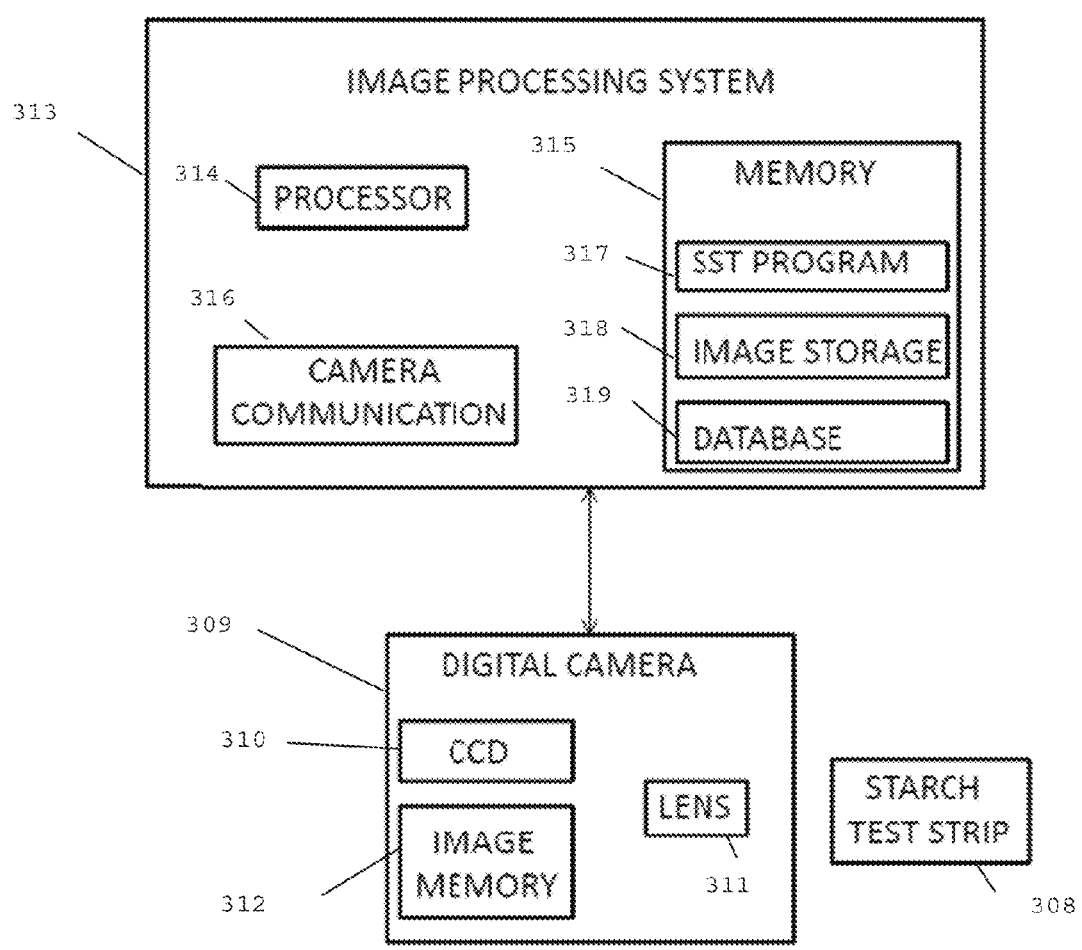
FIG. 3 illustrates an example of an SST system embodiment that images starch on a starch tape to perform a sweat test.

FIG. 3 illustrates an example of an SST system embodiment that images starch on a starch tape to perform a sweat test. The illustrated system includes a starch test strip 308 (also referred to herein as tape). The test strip may be made from a transparent material, on which the starch may be applied. The system also includes a digital camera 309 used to focus on the test strip to detect the dark spots on the starch caused by the sweat water. The camera 309 includes, among other things, an imager 310, such as a CCD (charge coupled device) imager, a lens for focusing the image on the imager, and an image memory for storing images that are taken during the test. CCD sensors are capable of producing high-quality, low-noise images.

An image processing system 313, such as a programmed computer, may be used to communicate with the camera and download the pictures off of the camera. The image processing system 313 may also be used to control the timing of the images taken by the camera. The illustrated system 313 includes a processor 314, memory 315, and camera communication module 316 for communicating with the camera. The functions provided by the system 313 may be provided by hardware, software, and firmware. The memory 315 may be used to store a SST program or programs 317 used to perform the test and analyze the test results, an image storage 318 in which the images from the camera may be loaded, and a database 319 in which test results may be stored.

The system 313 may use the images to calculate the rate of spot expansion and the expanding spot area. The imaged spot area is a virtual two-dimensional image. The rate of spot expansion determined from the two-dimensional images is converted to a sweat rate (volume over time) for each individual SG. For example, the sweat rate may use the units nanoliters/minute. The expanding area determined from the two-dimensional images is converted to a sweat volume for each individual SG. For example, the sweat volume may be given in nanoliters.

The system 313 may also be configured to determine SG density (SG number/area) and distribution of secreting SGs. Denervated SGs do not secrete. They leave detectable voids in the pattern. Data may be transferred to a database for final calculations and conversions as predetermined by appropriate camera calibrations. The process may be performed one or more times, and the results compared for SG number, distribution and other results as a safeguard of data collection and to assure that pilocarpine stimulation was consistently high, indicating that the test was applied correctly.

The SST may report SG number and distribution, sweat rate and volume for each of over 200 SGs, plus total rate and volume per skin area. The SST information reflects functional events that occur at the single gland level. Each SG has its individual rate and volume. Additionally, the number and distribution of the SGs that are secreting sweat water, the recruitment and sweat flow characteristics also may be determined.

As identified above, SST uses starch-coated transparent tape placed on iodine-coated skin. The tape forces the sweat droplets to flow centrifugally in a flat, expanding spot. As the sweat is limited to an expansion in virtually two dimension and is generally prevented from expanding in a third dimension, the thickness of the expanding spot is generally constant and the spot area is proportional to the sweat volume from the same SG. Each of the enlarging sweat spots may be identified and imaged many times during the test. Spots may be counted and sweat rate and sweat volume may be calculated for each SG. FIGS. 4A, 4B, and 4C illustrate images taken early in the sweat test, in the middle of the sweat test, and late in the sweat test. It can be seen that there are very few dark spots early (FIG. 4A), but that the dark spots grow (FIG. 4B) and merge with adjacent dark spots (FIG. 4C).

Figure 5A:
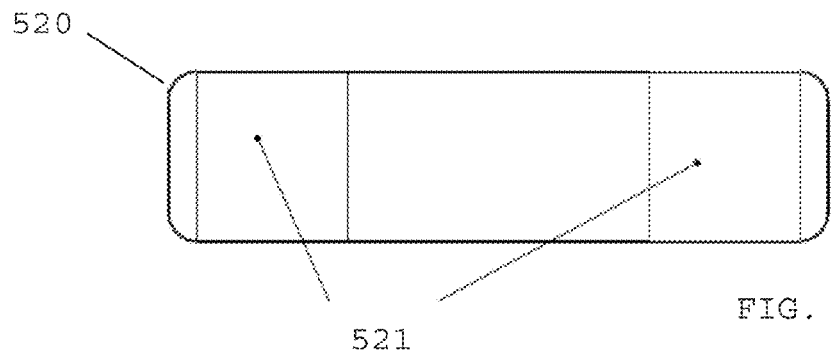
FIGS. 5A-5C illustrate planar and side views of an embodiment of starch test strip.
Figure 5B:
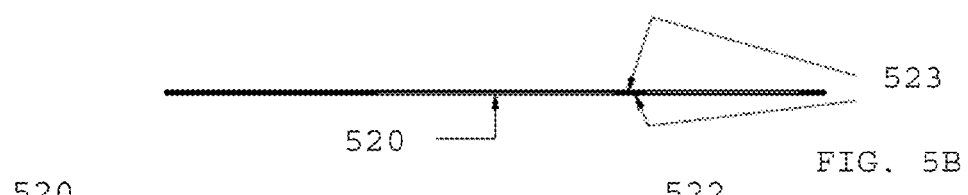
Figure 5C:
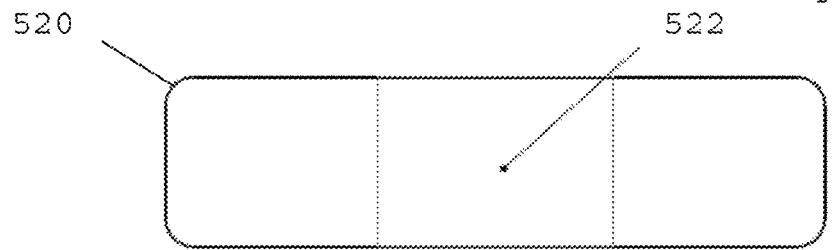
Figure 5D:
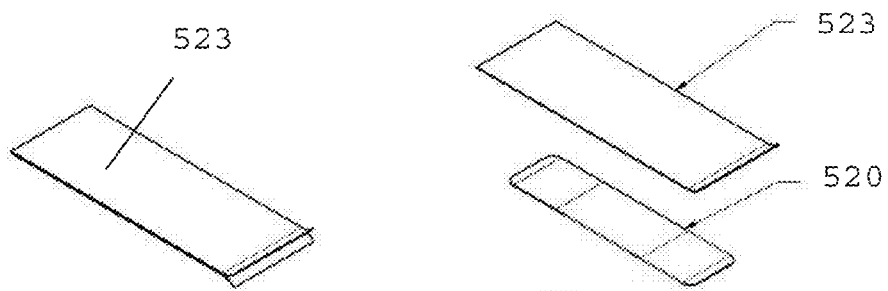
FIG. 5D illustrates a perspective view of the completed package, and FIG. 5E illustrate an exploded view of the packaged test strip.
Figure 5E:
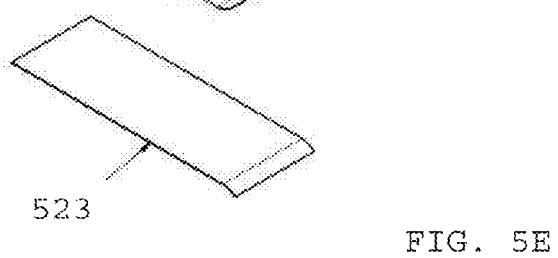

FIGS. 5A-5C illustrate planar and side views of an embodiment of starch test strip, FIG. 5D illustrates a perspective view of the completed package, and FIG. 5E illustrate an exploded view of the packaged test strip. One side of the test strip 520 includes two adhesive regions 521 positioned to be used to attach the test strip over the opening of the camera and to position the starch 522, centrally applied on the other side of the test strip, in line with the camera opening. Protective liners 523 may be attached to the test strip to protect the test strip before use. The test strip may be completely transparent, or the test strip may be transparent only where the starch is applied. There are a number of ways to create these strips. One way of placing starch on the strip is to run a web of tape through a trough of starch, and the remove the excess. For example, the web of tape may be unwound from an unwind roll to a first idler roll at a first end of the trough, and then to a second idler roll at a second end of the trough, and then out of the trough and up toward a rewind roll. Excess starch may be removed from tape using a vacuum, using a blower, by scraping, or a combination of methods. Other process may be implemented to deposit a desired amount at a desired location on the tape.

The system is designed to provide a high resolution image for use to accurately detect these dark spots. The starch tape is attached at a fixed distance from the camera lens. In some embodiments, the camera uses a wide angle lens with a short focus length. For example, the SUNEX DSL944 lens may be used. This lens is a multi-element glass lens that provides high resolution up to 8M CCD/CMOS imagers with a format size of ½.5 inch. The lens has an overall length from lens front physical surface to the image plane (the starch tape) of 11.3 mm, and an f-stop of F/2.8 with a long depth of focus.

Figure 6A:
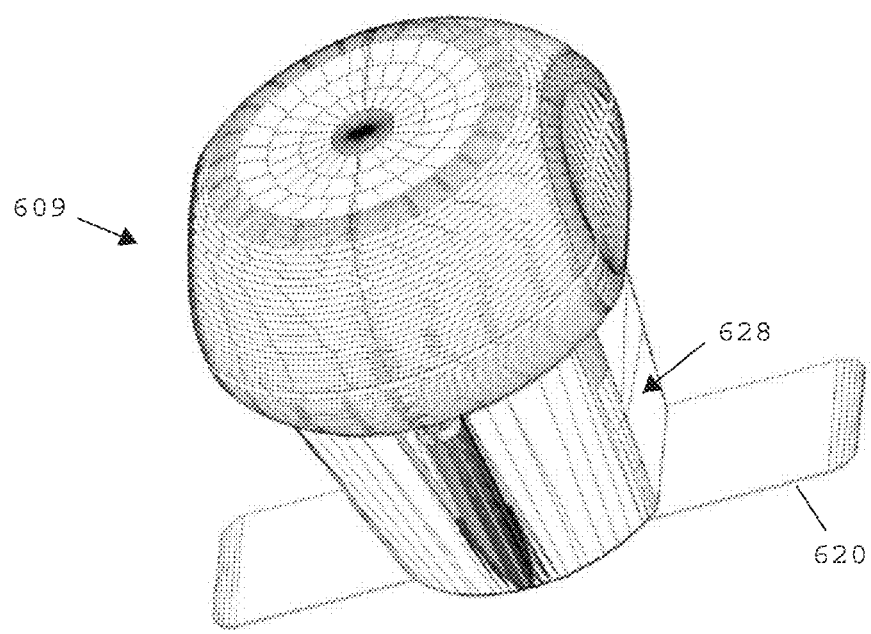
FIGS. 6A-6B illustrate perspective views of the camera with a starch tape placed over a camera opening.
Figure 6B:
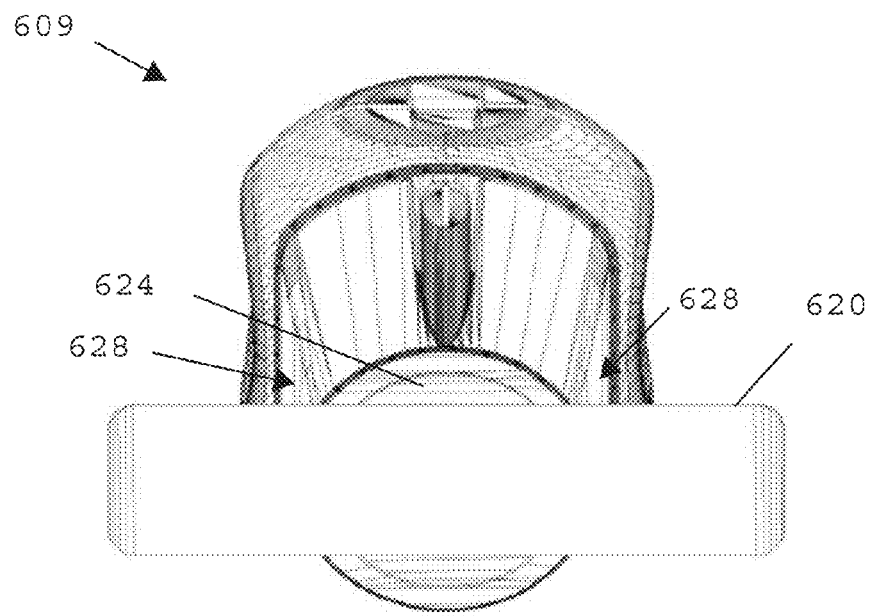
Figure 6C:
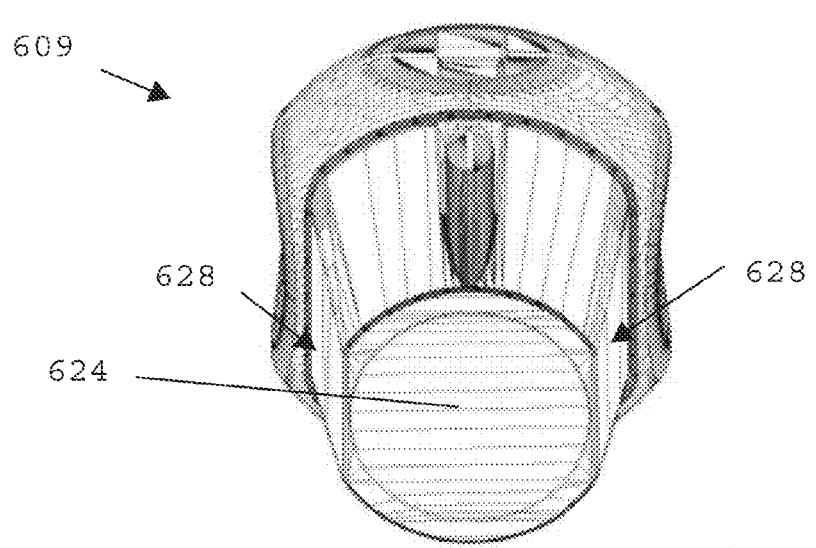
FIG. 6C illustrate the view of FIG. 6B without the starch tape to show a transparent window.
Figure 6D:
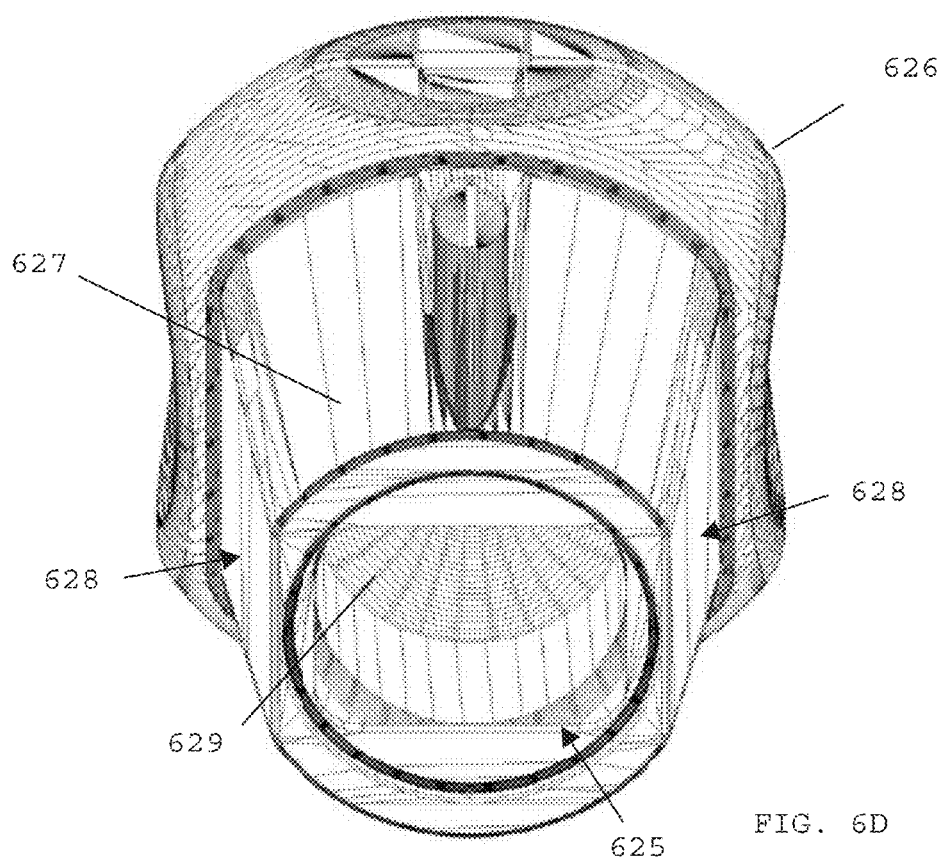
FIG. 6D illustrates the view of FIG. 6D without a transparent window and thus shows the camera opening.

FIGS. 6A-6B illustrate perspective views of the camera 609 with a starch tape 620 placed over a camera opening; FIG. 6C illustrate the view of FIG. 6B without the starch tape to show a transparent window 624, and FIG. 6D illustrates the view of FIG. 6D without a transparent window 624 and thus shows the camera opening 625. The housing of the camera 609 includes a cap 626 which houses the camera component and lens. The cap 626 also has a shape to function as a handle for a user to place the camera against the test subject. The housing of the camera 609 also includes a nose portion 627 which has the camera opening 625 on the end of the nose portion 627. The nose portion may also include other components such as a diffuser 629. The nose portion 627 may be screwed or otherwise fastened to the cap 626. The nose portion 627 may have flat surfaces 628, against which the adhesive portions of the test strip 620 may be pressed. Thus, the test strip 620 may be placed over the camera opening, and the ends of the test strip 620 may be folded back onto these flat surfaces 628. The camera structure is designed so that the image plane of the lens is at the end of the nose portion where the tape is attached.

Figure 7:
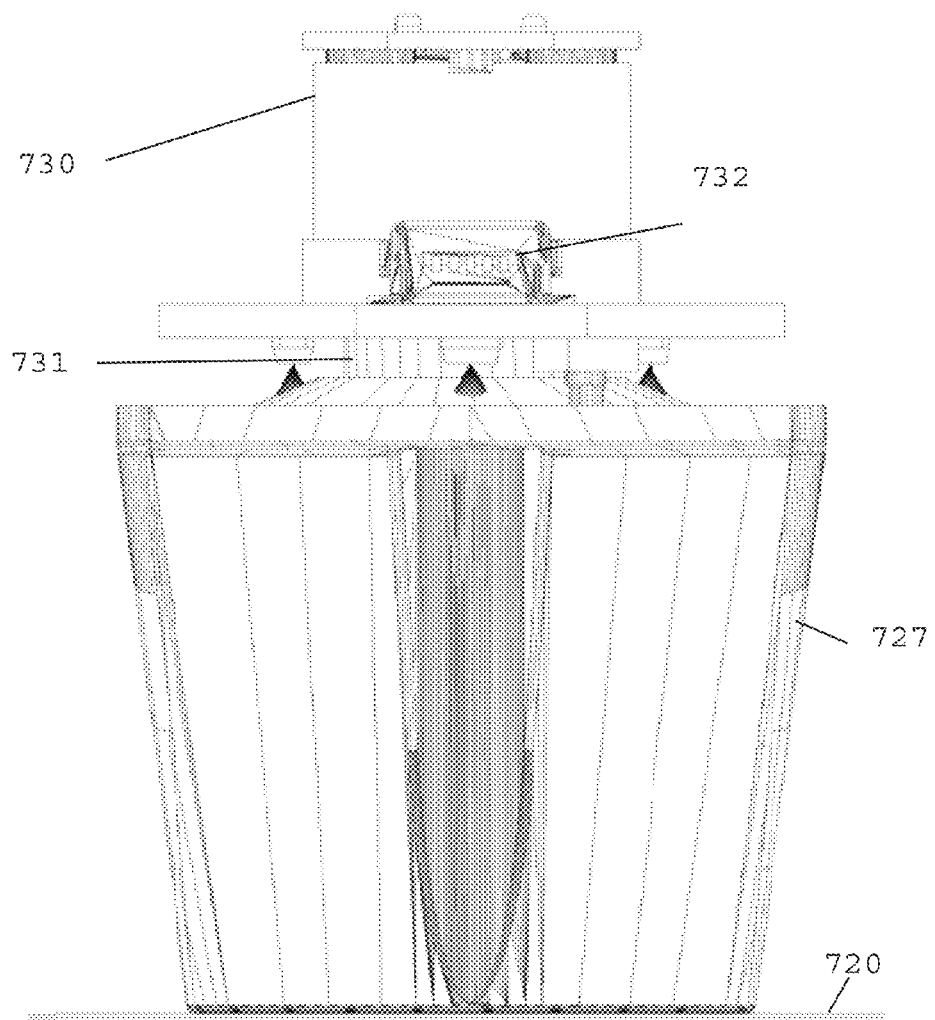
FIG. 7 illustrates a side view of the camera, without the cap, exposing the camera component, which includes the digital imager, and the lens.
Figure 8:
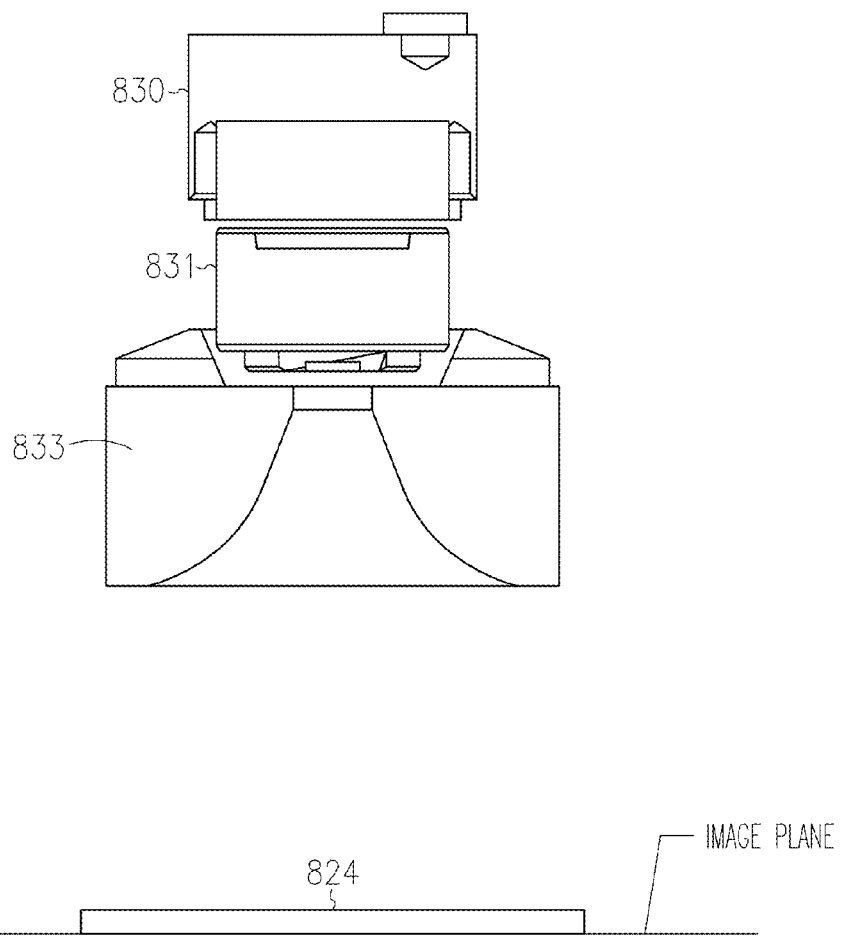
FIG. 8 generally illustrates the fixed distance between the camera lens and the test strip (image plane).

FIG. 7 illustrates a side view of the camera, without the cap, exposing the camera component 730, which includes the digital imager, and the lens 731. The illustration also shows a communication port 732 to receive a communication cable for use to communicate between a computer and the camera. However, the communication is not limited to cable connections, as wireless communication is also possible. The nose portion 727 allows a test strip 720 to be quickly placed on the image plane of the lens 731, and still obtain a high resolution, focused image. FIG. 8 generally illustrates the fixed distance between the camera lens 831 and the test strip 820 (image plane). The figure also illustrates the camera component 830, the diffuser 833, and the transparent window 824 at the end of the nose portion.

Figure 9:
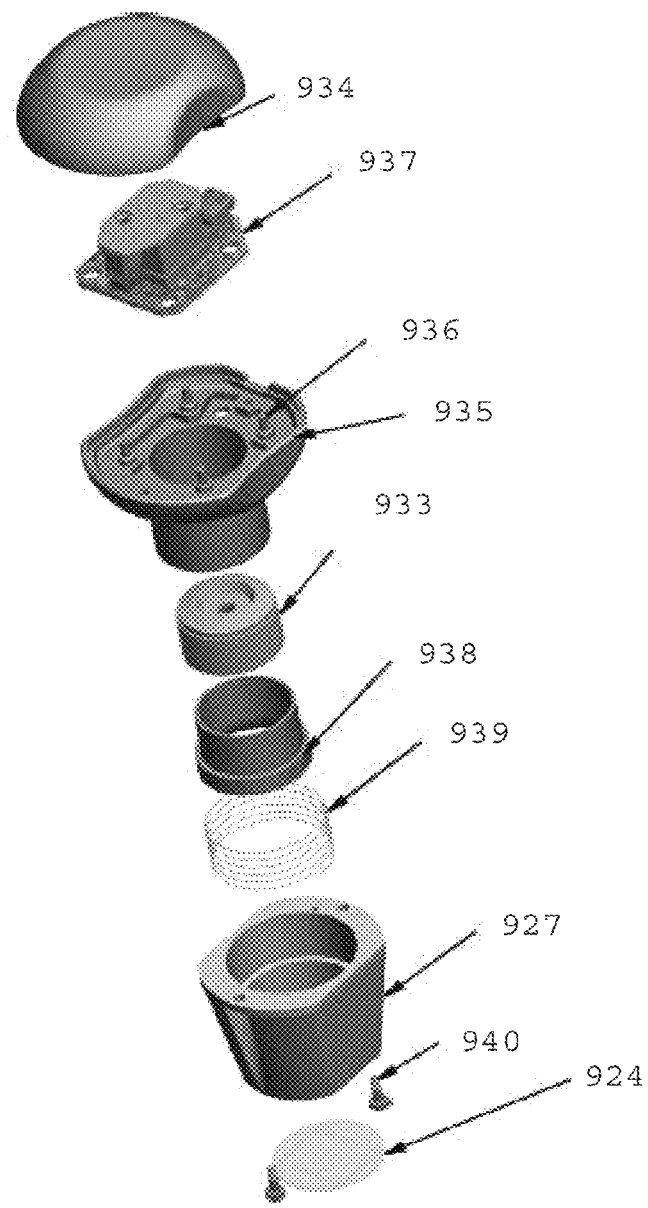
FIG. 9 illustrates an exploded view of an example of the digital camera.

FIG. 9 illustrates an exploded view of an example of the digital camera. The cap of the housing may be formed by a top housing component 934 and a bottom housing component 935, which may be attached together using screws 936. Together, the top and bottom housing components 934 and 935 form a cap that houses the camera circuit card assembly 937. This view also illustrates the diffuser 933, sleeve 938, spring 939, nose portion 927, transparent window 924 and shoulder bolts 940 used to connect the nose portion 927 to the bottom housing component 935. The spring 939 presses against the sleeve 938 and the nose portion 927, which along with the use of the shoulder bolts 940 allow some give when the nose portion 927 is pressed against the test area of the test subject.

Figure 10:
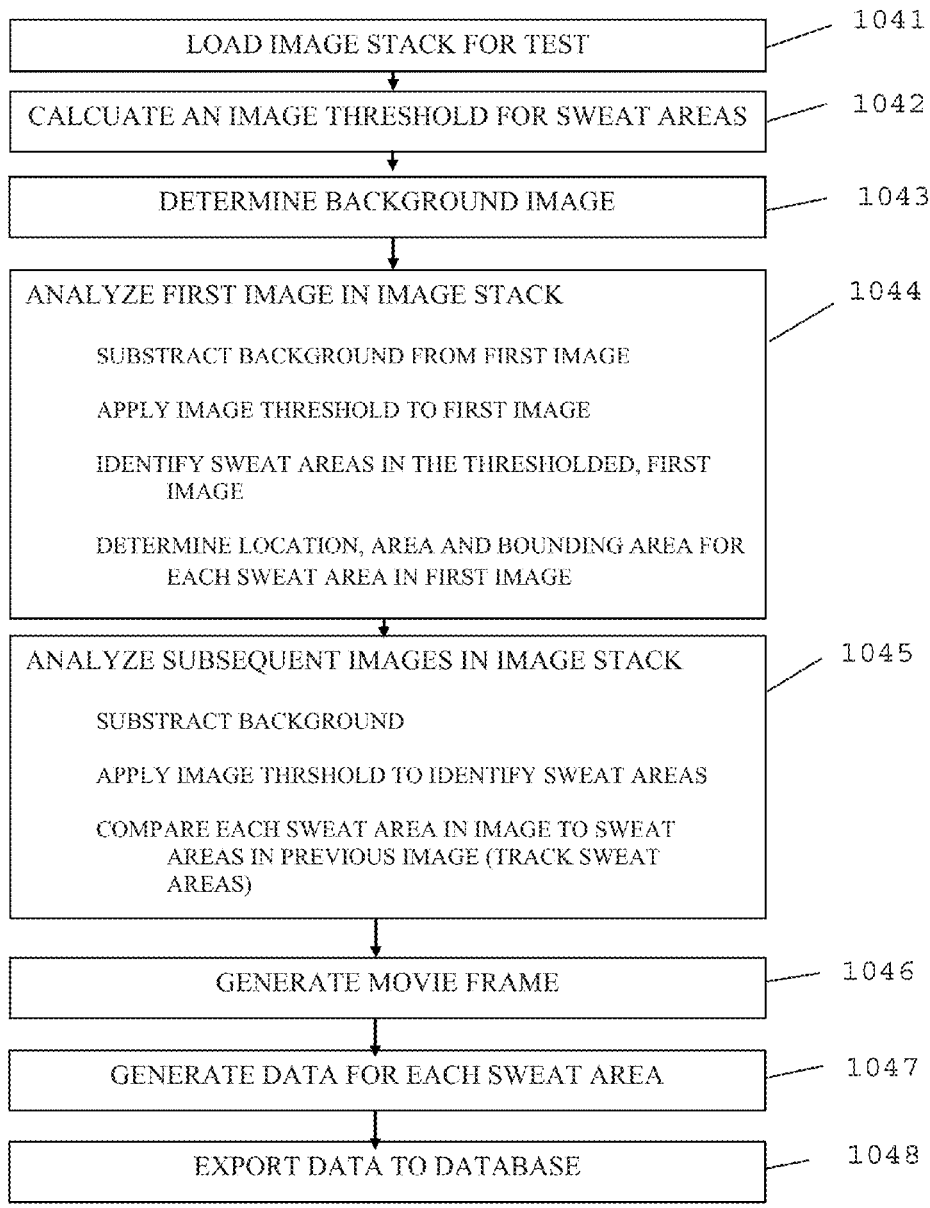
FIG. 10 illustrates a flow diagram of a process for analyzing the images taken during the course of the test.

FIG. 10 illustrates a flow diagram of a process for analyzing the images taken during the course of the test. For example, a series of 1 to 5 images may be taken every second for a duration of about 60 to 90 seconds. In an example, these images are initially stored in the camera, and then loaded into the image processing system for analysis.

At 1041, the image stack is loaded from the camera memory into the memory of the image processing system. At 1042, the image processing system calculates an image threshold for use to determine whether a given pixel represents a sweat area. For example, an image in the middle of the stack is used to generate a threshold. This image is expected to include a number of sweat areas of a relatively large size, but before the sweat areas start to merge with each other. The threshold calculated is dependent on which algorithm is used (SIS, Otsu, Local, or Simple fixed). At 1043, a background image is created from the first image in the image stack. This background image is used to subtract the constant portions of the picture to provide further contrast between the sweat areas and the areas without sweat. The first image has the fewest sweat areas, and thus is expected to mostly represent background. A smoothing process is performed on the first image to create the background image. For example, the first image may be shrunk to ¼ size, a Gaussian blur filter may be applied a number of times (e.g. 5 times) to the shrunken image, and a 3×3 mean filter may be applied to the shrunken image. The 3×3 image uses the average of 9 pixels to determine the value of the pixel in the center of the 3×3 block of pixels. The image may then resized back to original size to be used as the background image. The result is a smooth background.

The first image of the image stack is analyzed at 1044. For example, the background image may be subtracted from the first image, and the resulting first image may then be thresholded using the threshold calculated above. Each pixel in the thresholded image either represents a sweat pixel or a pixel without sweat. This may be envisioned as a black and white image. The thresholded image may then be segmented into sweat areas (spots), and each spot may be identified with a number identifier. For example, the spots in an image may be consecutively numbered scanning the image from left to right and top to bottom. Each spot has an X,Y center location, area, and bounding rectangle. An area of the spot may be calculated from the camera pixel calibration (measured image size/number of pixels), and volume may calculated using a linear fit of area to volume, the slope and intercept that can be determined from an area to volume calibration. Both of these calibrations are further described below.

The subsequent images of the image stack are analyzed at 1045, where the following may be repeated for each analyzed image. The background image may be subtracted from the analyzed image, and the resulting image may then be thresholded using the threshold calculated above. The thresholded image may then be segmented into sweat areas (spots), and each spot may be identified with a number identifier. Each spot is compared to the spots in the previous image so they may be tracked from image to image. If the current spot covers the same pixels as a spot from the previous image, its identifier is changed to that from the previous image. If the current spot has a number that was already assigned in the previous image, but does not overlap a previous spot, its identifier is changed to an unused identifier. If the current spot covers more than one spot from the previous image, its identifier may be changed to the lowest overlapping identifier number from the previous image, or the new spot may be considered merged and its identifier changed to a range of identifiers reserved for merged spots.

At 1046, the images may be combined into a movie frame. The spots may be color-coded by number, with merged spots being colored gray. Once all frames are processed, a list of spots may be generated which includes the spot identifier, start frame, stop frame, start area in mm, stop area in mm, micro liter change, and rate per second. Additional data may be recorded as well, such as data pertaining to intermediate frame(s) between the start and stop frames. This data may be exported to a database.

If the spot area has increased, a value for the area (in pixels for example) may be stored in a table corresponding to its identifier and the frame in concern. If two sweat areas have merged, a new identifier may be assigned and the area is not calculated as it would show a (wrong) sharp jump in the area. The number of uniquely identified spots (sweat areas) may be counted to identify the number of active SGs. Each sweat area, before merging with another sweat area, represents an active SG. The numbers of SGs per $cm^2$ may be derived from this SG count and from a camera calibration that identifies how many pixels fit in a given $cm^2$ area.

Also, a growth rate for each of sweat areas may be calculated. The nomenclature below uses "X" to refer to an earlier sweat area (e.g. from an earlier image frame) and uses "Y" to refer to a later sweat area (e.g. from a later image frame). The X image frame may be the first frame in which the sweat area appeared, and the Y image frame may be the last frame in the test or the last frame before the sweat area merges with an adjacent sweat area. For this X and Y, the rate can be calculated as the average rate for the test. However, the X image frame does not have to be the first image frame and the Y image frame does not have to be the last image frame. For example, as the rate of sweat production in a given SG may vary, it may be desirable to track the sweat rate of each SG throughout the course of the test or for a given portion or portions of the test. A rolling average of "n" images may be used. For example, an average of the sweat area for images 1-5 may be determined for image "3", and average of the sweat area for images 2-6 may be determined for image "4", etc. Larger values of "n" are less responsive to changes in the calculated rate, and smaller values of "n" are more responsive to changes in calculated rate.

Let $Ax$=area of the sweat area (pixels) at frame.

Let $Ay$=area of the sweat area (pixels) at frame $y$.

$n=y-x$=Number of frames.

Rate of Increase=$(Ay-Ax)/n$(pixels/frame).

The rate of increase maybe converted from pixels per frame to pixels per second using the number of frames that are imaged per second (f).

Rate of Increase=$(Ay-Ax)*f/n$(pixels/second)

Figure 11:
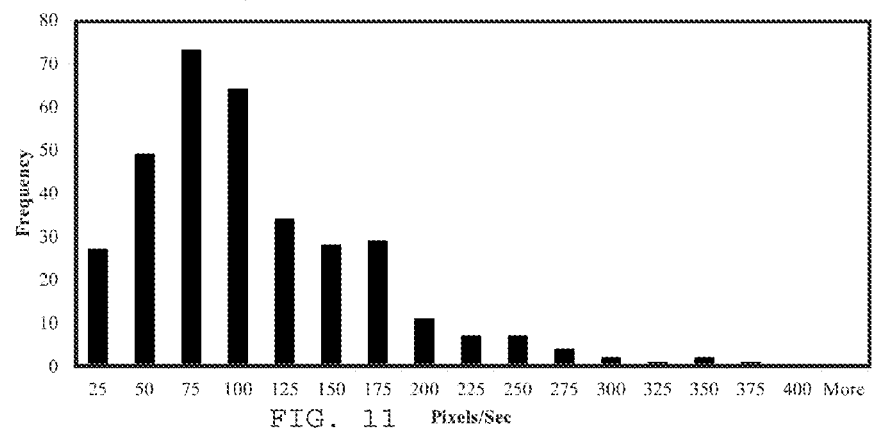
FIG. 11 illustrates a histogram that groups together sweat areas that grow at the same rate, as displayed by the rate of increase in area on the X axis and the number of sweat areas on the Y axis.

The sweat areas that grow at the same rate may be grouped together and plotted in a histogram with the rate of increase in area on the X axis and the number of sweat areas on the Y axis, as generally illustrated as an example in FIG. 11. If a SG does not sweat, a sweat area does not appear on the image frame and there is no record of that SG and that non-active SG is not counted. Correspondingly, the histogram has fewer frequencies overall. So a generally "low" histogram is an indicator of fewer functional SGs in the area imaged.

As the sweat is limited to a space near the skin by the transparent tape, the growth of the sweat area is generally constrained to growth in the generally two-dimensional region along the surface. The thickness of the layer of sweat on the skin is generally constant, and the volume (ml$^3$) of the sweat can be approximated as a linear function of the area (ml$^2$) of the sweat area. An example of a process for converting from an area to volume is provided below.

Each camera device is calibrated to determine the size of the pixels in the images taken by the device, which allows the pixels to be converted into μm. For example, an image may be taken of a micrometer area (e.g. a 4000 μm by 4000 μm area). The image may be opened in rendering software to determine the length of the area in both the X and Y directions (e.g. 608 pixels in both directions). This information maybe used to calculate the size of a pixel in microns (e.g. 4000 μm/608 pixels=6.57895 μm per pixel). That is, one pixel is equal to 6.57895 μm. A second calibration may be performed using a 250 μm by 250 μm area and a similar process may be performed to confirm the ratio between μm and pixels, thus providing a higher level of confidence in the calibrated values.

Figure 12:
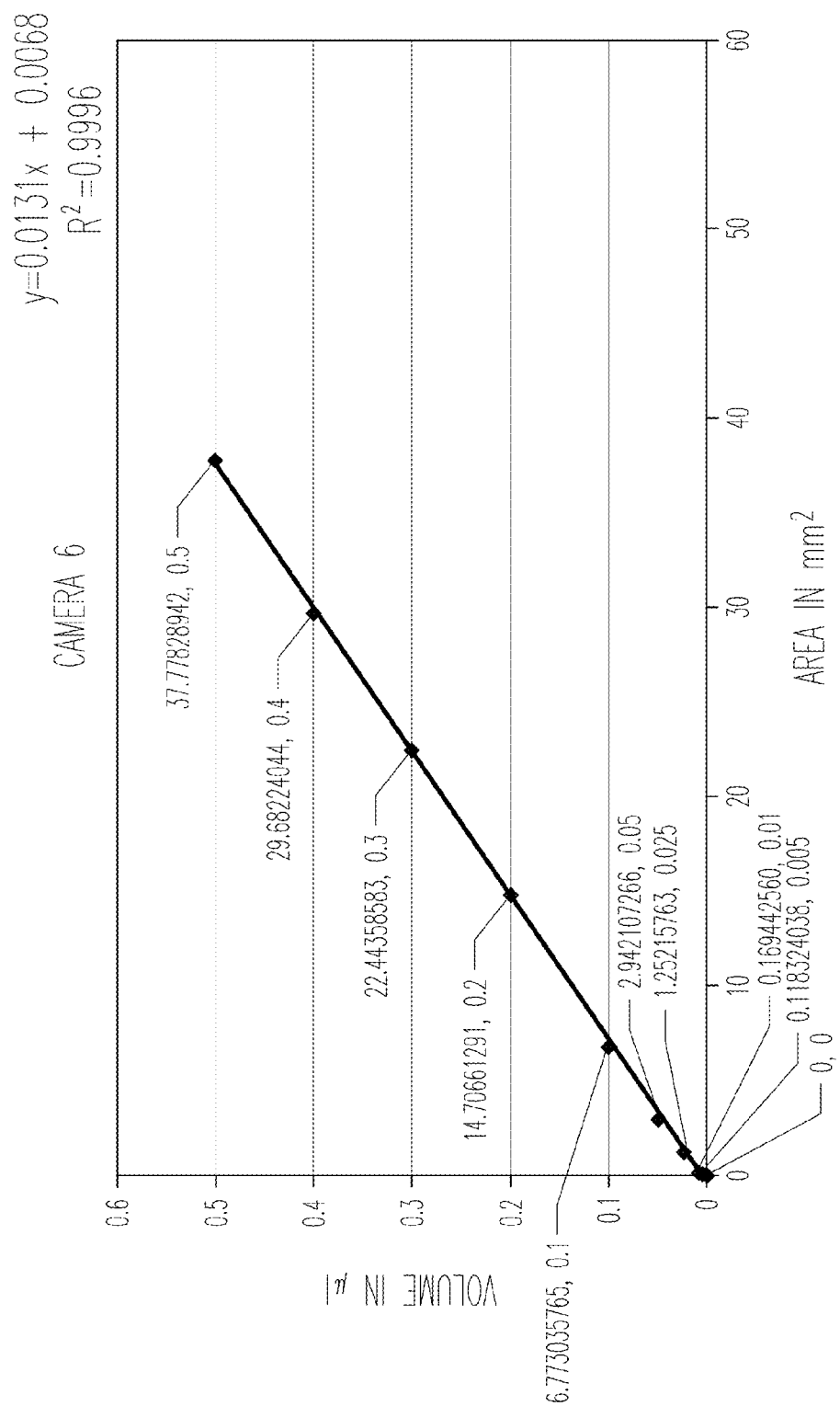
FIG. 12 illustrates a linear equation for converting sweat area to sweat volume derived from a calibration procedure.

The calibration procedure may continue to determine a linear relationship between the sweat area and volume. For example, a very accurate Hamilton pipette may be used to precisely measure volumes of iodine. The measured volumes range from 5 nanoliters (nl) to 500 nl, for example. Each known volume is measured multiple times (e.g. 20), and each one of those is placed on a starch coated tape, then quickly flattened with a clean glass slide and quickly imaged with the camera. The imaged drop may then be opened up in one or more image rendering software programs (e.g. image J and neurolucida). The pixel calibration may be entered (e.g. 6.57895 μm from above) and the area of the volume droplet may be measured in mm$^2$. Sampling each volume multiple times (e.g. 20) increases the sample and reduces error in the calibration procedure, as an average of many values may be determined for each volume. Each new camera device should be calibrated. A linear equation (y=ax+b, where Y represents volume and X represents area) may be derived from these plotted points, as generally illustrated FIG. 12. This linear equation functions as a conversion from a measure of area to a measure in volume. The conversion equation may be incorporated into the database along with an identifier of the corresponding camera that was calibrated. Thus, for a given sweat video imported into the database, the camera that was used for imaging may be identified to allow the database to convert the imaged areas into volumes, and to calculate sweat rate (e.g. nl/s). SG density (SGs/cm$^2$) may be determined from a count of sweat droplets within the whole imaged field and from the calibration of the camera.

Some SST embodiments use a nano grid of electrical conductors to test sweating function. This is a nano technology system that is designed to measure SG rate and volume, number of SGs and distribution pattern, which is faster and simpler than imaging the starch-coated transparent tape in the above described system. Furthermore, the nano grid may also be configured to analyze the content of the sweat.

Figure 13:
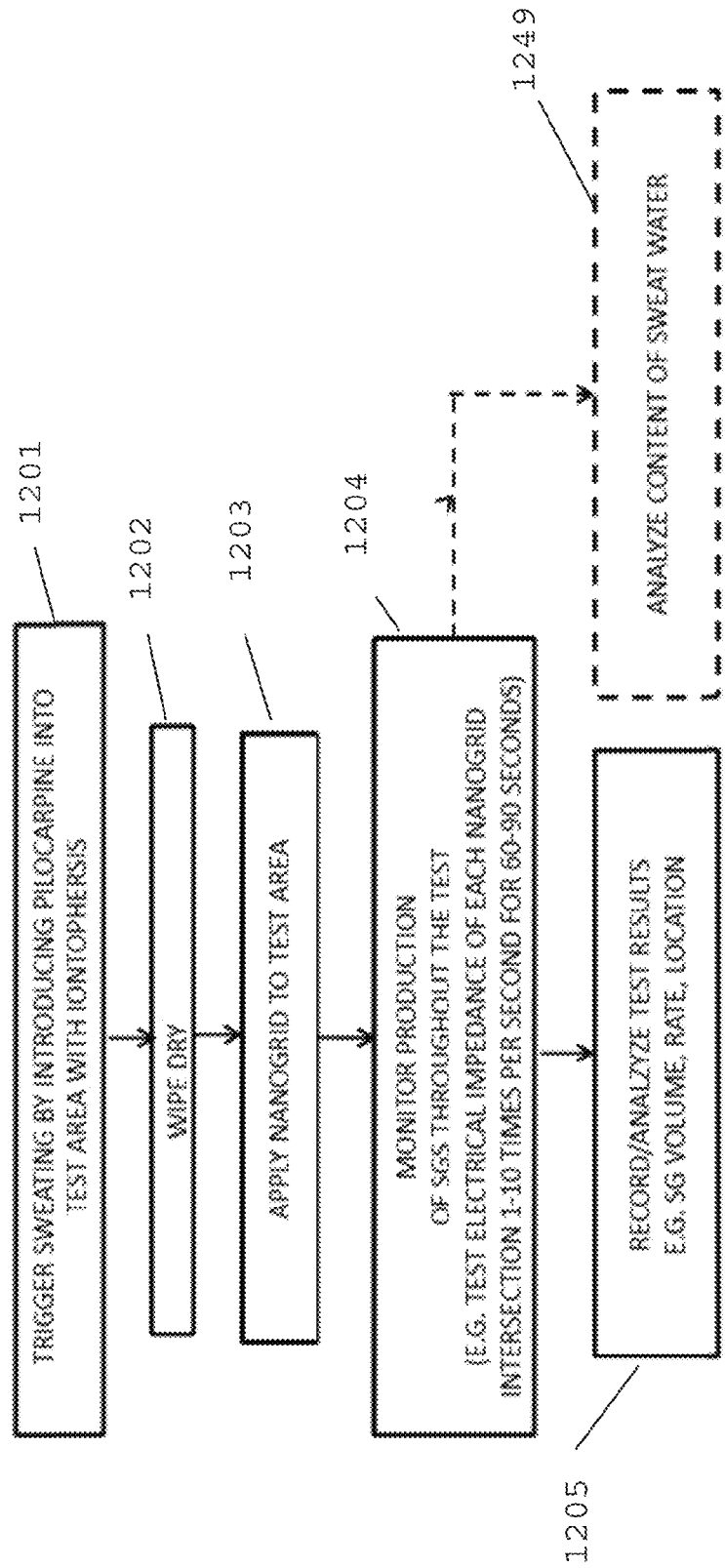
FIG. 13 illustrates an example of a nano grid embodiment that may be used to evaluate peripheral neuropathy to a sweat test.

FIG. 13 illustrates an example of a nano grid embodiment that may be used to evaluate peripheral neuropathy to a sweat test. At 1301, significant sweating at a test area on the skin of the patient is triggered or induced by introducing pilocarpine into the test area with iontophoresis, as was described above. After a short interval (often 10 minutes) after iontophoresis to assure the desired SG secretion, the skin is quickly wiped dry with a swift motion 1302, and the nano grid is immediately applied to the skin 1303. As sweat water begins to exit from each of the sweat pores within the tested area, the sweat water contacts the wires at the intersection, causing a significant drop in resistance. At 1304, the sweat production of the SGs are monitored throughout the test. For example, the electrical impedance of each nano grid intersection may be tested 1 to 10 times per second and may continue testing for 60 to 90 seconds. In some embodiments, the SST test may also analyze the content of the sweat water produced during the test 1349.

Figure 14:
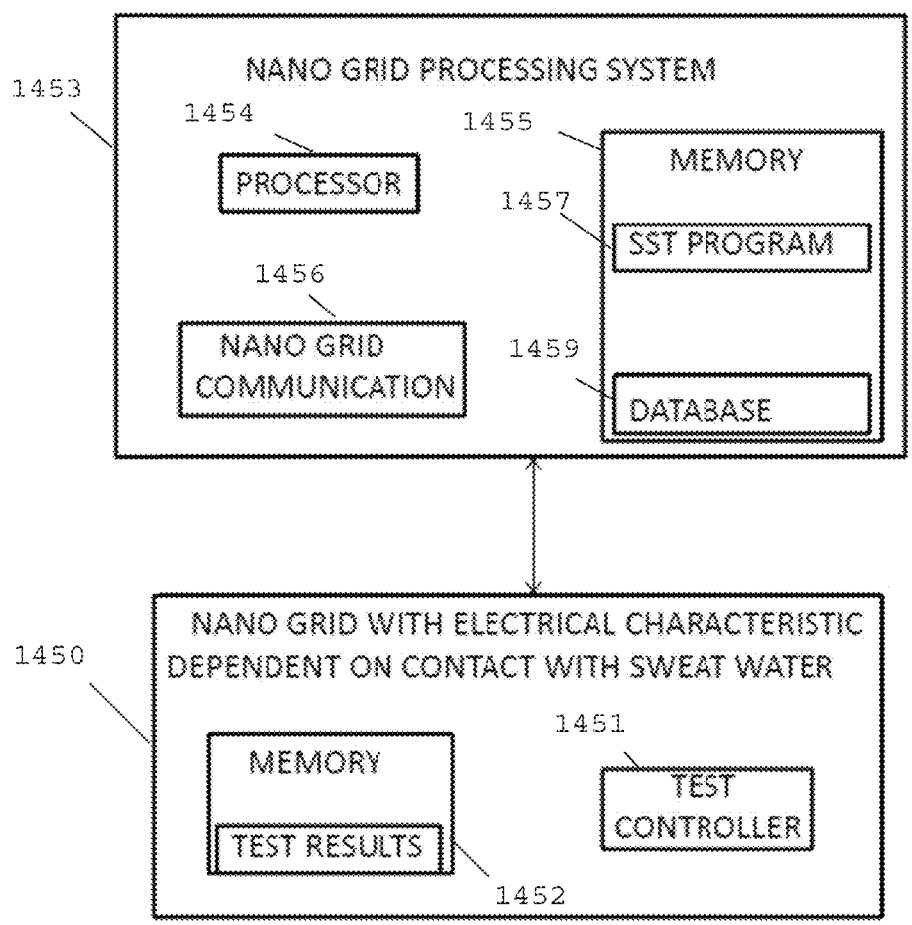
FIG. 14 illustrates an example of an SST system embodiment that uses a nano grid of electrical conductors to perform a sweat test.

FIG. 14 illustrates an example of an SST system embodiment that uses a nano grid of electrical conductors to perform a sweat test. The illustrated system includes a nano grid assembly 1450 that includes the grid of electrical conductors, and that further includes a test controller 1451 configured to test the nano grid and determine which intersections of the nano grid are in contact with the sweat water, based on a detectable electrical change in the wires. The nano grid assembly may also include a memory 1452 for storing test results during the course of a test. In some examples, at least some of these processes may be performed by the nano grid processing system.

The nano grid processing system 1453, such as a programmed computer, may be used to communicate with the nano grid assembly 1450 and download the test results from the memory 1452. The image processing system 313 may also be used to control the timing and procedure for testing the intersections. The illustrated system 1453 includes a processor 1454, memory 1455, and nano grid communication module 1456 for communicating with the nano grid assembly 1450. The functions provided by the system 1453 may be provided by hardware, software, and firmware. The memory 1455 may be used to store a SST program or programs 1457 used to perform the test and analyze the test results, and a database 1459 in which test results may be stored.

The system 1453 may use the test results to calculate the rate of expansion and the area of the sweat areas for various times during the test. Each intersection of the grid is analogous to a pixel of the imaged sweat area for the starch tape system described above. However, rather than showing a dark (or light) pixel for a corresponding wet area of the starch, a significant change in impedance at an evaluated intersection indicates that sweat has reached the intersection and is forming a conductive path between the intersecting conductors. The grid may be adhered to the skin, similar to the starch tape, to limit the growth of the sweat droplets to be in a narrow layer along the skin surface. Thus, an area to volume linear equation may be derived, similar to the approach described above. The pattern of voltage drops at multiple crossings of nanowires in the grid will provide continuous monitoring of the locations of the moving boundaries of nano liter drops. These will be proportional to the sweat rate of the underlying SGs.

Figure 15:
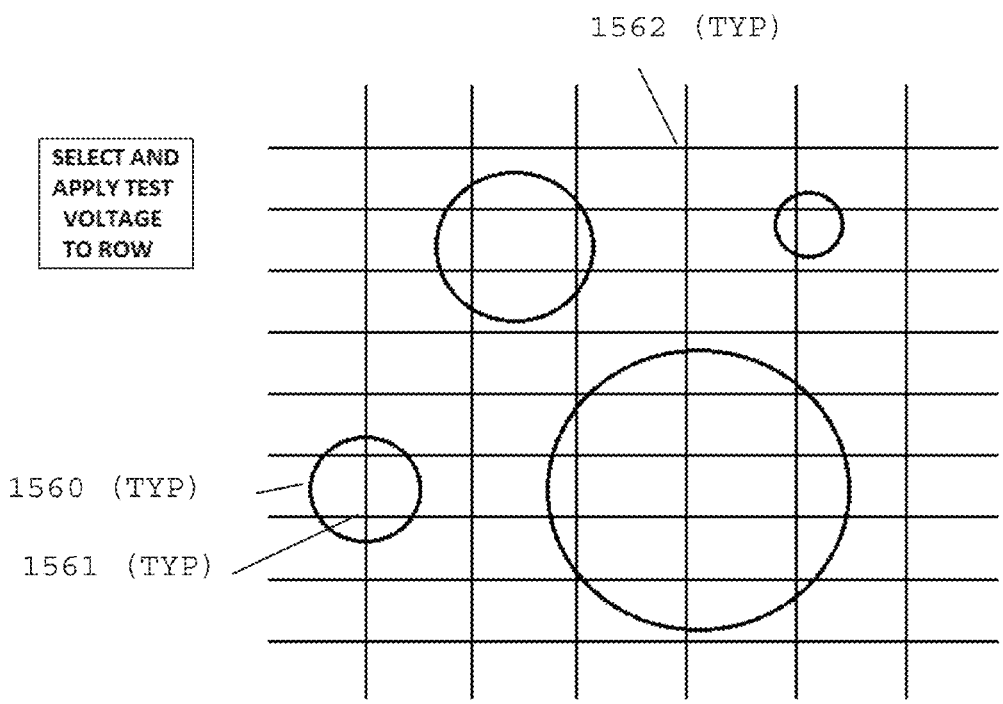
FIG. 15 illustrates sweat water from SGs, and further illustrates intersections in contact with sweat water, and intersections not in contact with sweat water.

FIG. 15 illustrates sweat water 1560 from SGs, and further illustrates intersections 1561 in contact with sweat water, and intersections 1562 not in contact with sweat water. Intersections 1561 have low impedance, and intersections 1562 have high impedance. These data points provided by the intersections are similar to the data points provided by pixel images. By way of example, the intersections may be scanned 1-10, or more, times per second. The scanning method may simply be selecting a row from top to bottom, and for each selected row selecting a column from left to right. Other scanning techniques may be implemented. A standing voltage may be applied to the selected row, and the electrical potential on the selected column may be read to determine whether the intersection is in contact with sweat water. The electrolyte laden sweat water is conductive. Expansion of the continuously secreted sweat water contacts the conductors of the grid. This allows continuous monitoring of the locations of the moving boundaries of nanoliter drops. These will be proportional to the sweat rate of the underlying SGs. Thus, the system may be used to provide similar data as provided by systems that use starch tape. Example of this data include SG density (SG number/area) and distribution of secreting SGs, sweat rate and volume for each of over 200 SGs, plus total rate and volume per skin area.

Figure 16:
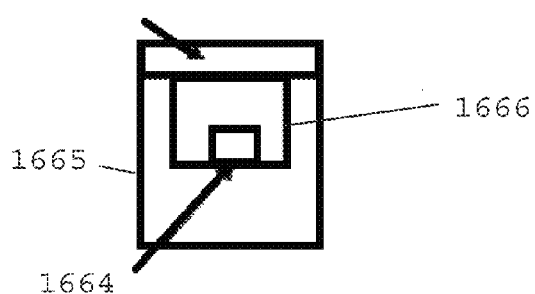
FIG. 16 illustrates an example of a structure of an intersection of the array.

FIG. 16 illustrates an example of a structure of an intersection of the array. Two sets of conductors may be formed to provide a layered structure. In the illustrated example, the conductors within each set run parallel to each other and perpendicular to the conductors in the other set. The illustrated intersection shows a top conductor 1663 that is part of a top set of conductors and a bottom conductor 1664 that is part of a bottom set of conductors. An insulator 1665 generally separates the lines from each other. The insulator may be formed as one or more insulators during fabrication of the nano grid. A pocket 1666 of air is created at every metal line intersection by etching holes through the insulator. Thus, at each intersection, the conductor from one layer is separated from the conductor from the other layer by air, which is an insulator. Thus, the impedance between the two lines is quite large. However, the sweat water is conductive. Thus, when sweat water enters the pocket 1666 and contacts both conductors 1663 and 1664, the impedance between the conductors drops significantly. It is noted that if a standing voltage is applied to one of the conductors, then the conductors are driven with a direct current (DC) and the impedance between the conductors can be referred to as the electrical resistance between the conductors.

The device works by measuring the electrical resistance between the conductors at each intersection, and sweat is detected by a dramatic drop in resistance. The device may exhibit a resistance of about $10^{10}$ to $10^{11}$ ohms between the conductors. When normal saline is applied the resistance drops significantly (e.g. eight orders of magnitude to about 800 ohms). The response time is of order milliseconds.

The device can be rinsed in water and reused indefinitely. Water adsorption due to room humidity or incomplete drying after cleaning will not change the measurement significantly since it is the ions in sweat that actually conduct current.

The ends of the conductors may be connected to multiplexers so that a digital signal can be used to determine the row and column of interest and the resistance can be read back. A single multiplexer may be used to provide control for both the rows and columns of the array. The multiplexor(s) functions as a row select and a column select, to allow electrical connections between a node with a standing voltage and one of the selected conductors and another connection between a sensor and the other of the selected conductors.

Figure 17:
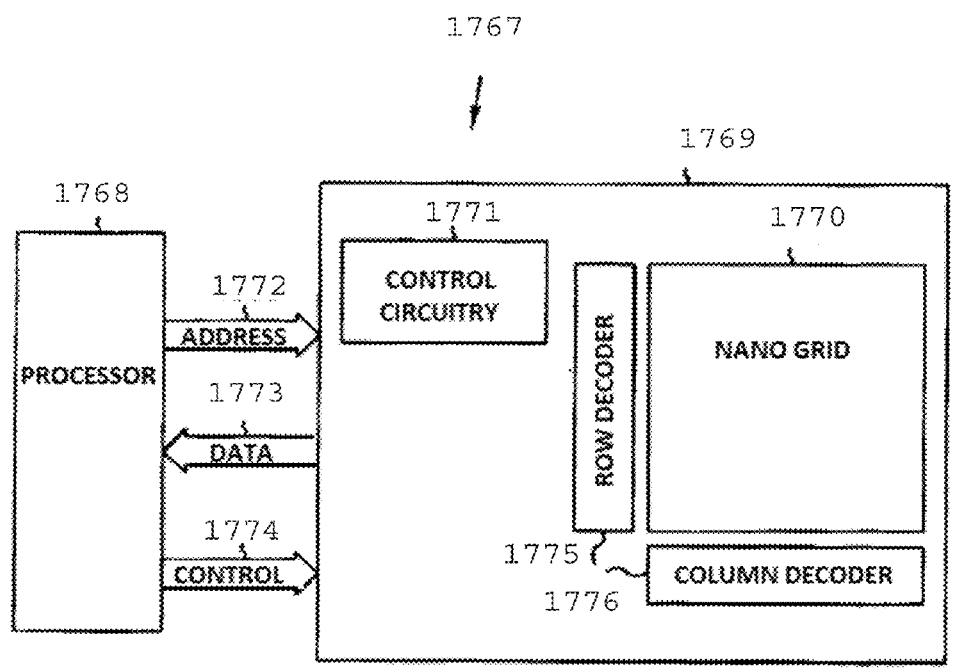
FIG. 17 illustrates an example of a system for reading the electrical resistance of the nano grid intersections.

FIG. 17 illustrates an example of a system for reading the electrical resistance of the nano grid intersections. The system 1767 includes a processor 1768 and a sensor device 1769. The sensor device 1769 includes a nano grid 1770 and control circuitry 1771, and is connected to the processor through an address bus 1772, a data bus 1773 and a control bus 1774. In a read operation initiated by the processor, address information and control information are provided to the sensor device. Row and column decoders 1775 and 1776 use this information to select the row and column to be tested. The resistance determined for the tested intersections may be communicated back to the processor 1768 via the data control bus 1773.

The nano grid may also be configured to identify and quantify the concentrations of the large number of substances in sweat water. These include electrolytes, sugars, peptides, proteins, including antibodies and antibiotics and lipids. Many of the same components are present in blood and extracellular fluid and some in urine. Thus, the nano grid system may be used to quantify SG function to detect peripheral neuropathy early and to analyze electrolytes, peptides and other body constituents routinely sampled in blood and urine. The system takes advantage of the location of SGs on most of the body surface where sweating can be tested non-invasively and inexpensively without patient risk.

As discussed above, sweating provides an early direct measure of nerve abnormalities secondary to chemotherapy induced peripheral neuropathy (CIPN), diabetic, alcoholic and other neuropathies using a simple procedure. Further the content of sweat can also provide important diagnostic clues. Sweat contains electrolytes, peptides/proteins, carbohydrates and other analytes, which may useful with patients suffering from several disorders such as, by way of example and not limitation, diabetes (glucose), cystic fibrosis (chloride), uremia, intoxication or prostatic cancer (prostate stimulating antibody). The device may be used to provide an early detection of exposure to neurotoxins in general.

The nano grid may be integrated with sensors to measure the concentration of selected analytes in the sweat. By way of example and not limitation, chlorine is the marker for the presence of cystic fibrosis. ChemFETs are one example of such a sensor. The ChemFET is similar to a conventional MOSFET, but an organic ion sensitive membrane such as polyurethane, silicone rubber, polyamide, or polystyrene is used in place of the gate electrode. This attachment can be done mechanically or chemically. The choice of membrane and its treatment depend on the target to be sensed.

Figure 18:
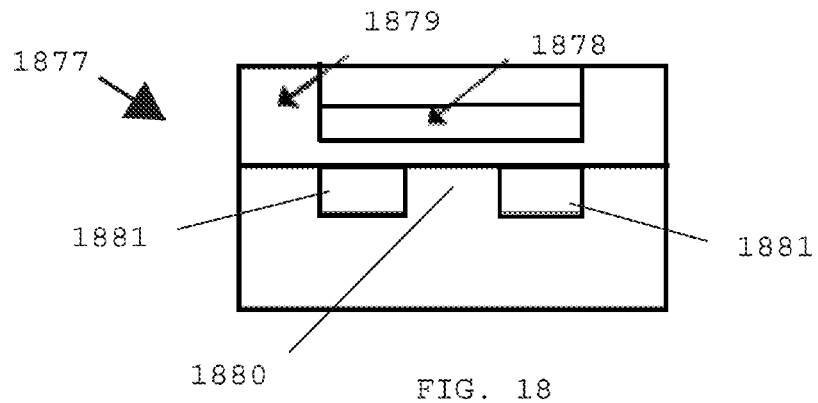
FIG. 18 illustrates a ChemFET.

A MOSFET functions as a switch, as an electrical potential at the gate controls whether current flows between source/drain regions of the MOSFET. The ChemFET operates similarly, except that analyte ions provide the gate control for the FET. FIG. 18 illustrates a ChemFET 1877. When the analyte ions diffuse through the membrane 1878 and reach the surface of the gate insulator 1879, their charge creates an electric field which modulates the carrier density on the surface of the FET and induces a current in the channel 1880 between the source/drain regions 1881 that is easily detected. ChemFETs have been demonstrated that are sensitive to many ionic species including Na+, K+, Ag+, and transition metal cations. Highly specific biological compounds can be incorporated as well for the detection of various organic species. These include glucose oxidase for the detection of glucose, and penicillinase for the detection of penicillin.

The examples provided above describe systems and methods for evaluating SGs in a test area. The size of the test area may be about 2 $cm^2$, which depending on skin location, contains about 200 SGs. Larger areas would test a larger number of SGs and smaller areas would test a smaller number of SGs. Also, the number varies depending upon the location on the body being tested. These examples also illustrate means for evaluating discrete points within the test area to determine whether there is sweat at that point. These discrete points may be referred to as "pixels" whether the discrete points are in a digital image or whether the discrete points are intersections of the nano grid. Each of these discrete points provides a data point for the test area. The distribution of these data points is appropriate to monitor the sweat production of individual SGs within the test area. The number of data points determines the amount of detail ("resolution") for the test.

By way of example and not limitation, a 5 MP camera may be used to image a 2 cm×2 cm region, and the resulting image includes sufficient detail to monitor the sweat production of individual SGs. However, other imaging configurations are possible that still provide the required resolution to monitor the production of individual SGs. Similarly, the nano grid configuration also provides sufficient data points ("intersections") to monitor sweat production of individual SGS. For example, if a 2 cm×2 cm test region is used, one million data points could be obtained by placing 1,000 equally-spaced nanowires in each layer (1,000×1,000=1,000,000). The resolution can be controlled by controlling the number and spacing of the nanowires. The size can be scaled down according to the ability to fabricate the nano grid of nano wires. However, it is not necessary to make the test area square. For example, it may be desirable to fabricate the grid to provide the desired area for testing, but with an aspect ratio between 3:1 to 10:1. For example, 1,000 equally spaced wires in one layer and 5,000 equally spaced wires in the other layer can provide 5 million data points. If the spacing between wires is the same for each layer, the nano grid has a 5:1 aspect ratio.

One of ordinary skill in the art will understand that the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for performing a sweat test; comprising:
triggering sweating in a test area of a test subject;
drying the test area, and applying a test device on the test area, wherein applying the test device includes applying a nano grid of nanowires on the test area;
monitoring, using the test device, sweat production of individual sweat glands (SGs) within the test area to provide test results for each functional SG in the test area, including measuring a change in electrical characteristics of the nano grid of nanowires, wherein:
the nano grid includes intersections of nanowires and includes air pockets configured to expose nanowires at each of the intersections, and the air pockets are configured to allow sweat water to enter and contact the nanowires; and
measuring a change in electrical characteristics of the nano grid of nanowires includes for each of the intersections detecting whether an impedance between the nanowires has dropped significantly, indicating that sweat water has entered the pocket and is in contact with the nanowires at the intersection; and
recording the test results for each functional SG in the test area.

2. The method of claim 1, wherein triggering sweating in the test area includes introducing pilocarpine into dermis of the test subject using iontophoresis.

3. The method of claim 1, wherein:
applying the test device further includes applying sensors on the test area with the nano grid of nanowires, wherein the sensors are configured to sense sweat content, the method further comprising evaluating sweat content using the sensors.

4. The method of claim 3, wherein applying sensors includes applying chemical field effect transistors (Chem-FETs).

5. A system for performing a sweat test on a test subject, comprising:
a test device configured to be applied to a test area on the test subject, wherein the test device is configured to detect sweat production of individual sweat glands (SGs) within the test area, wherein the test device includes a nano grid of nanoconductors and circuitry configured to test conductivity of the nano grid to detect sweat production of individual SGs in the test area, wherein:
the nano grid of nanoconductors includes a first level of parallel nanoconductors and a second level of parallel nanoconductors, the first and second levels of nanoconductors crossing at a plurality of intersections, the first and second levels of nanoconductors generally separated by an insulator, the insulator including an air pocket at the intersections, each air pocket exposing one nanoconductor in the first level and one nanoconductor in the second level; and the circuitry includes circuitry configured to test electrical impedance between two nanoconductors at each of the air pockets; and a processing system configured to analyze the detected sweat production, provide test results for each functional SG in the test area, and record the test results for each functional SG in the test area.

6. The system of claim 5, wherein in addition to the nano grid, the test device applied to the test area of the test subject further comprises at least one sensor configured to sense content of sweat water.

7. A system for performing a sweat test on a test subject, comprising:

a nano grid of nanoconductors and circuitry configured to test conductivity of the nano grid to detect sweat production of individual SGs in the test area, wherein:

the nano grid of nanoconductors includes a first level of parallel nanoconductors and a second level of parallel nanoconductors, the first and second levels of nanoconductors crossing at a plurality of intersections, the first and second levels of nanoconductors generally separated by an insulator that has an openings to expose the intersections to produced sweat; and the circuitry includes circuitry configured to test electrical impedance between two nanoconductors at the intersections; and a processing system configured to analyze the detected sweat production, provide test results for each functional SG in the test area, and record the test results for each functional SG in the test area.

8. The system of claim 7, further comprising at least one sensor configured to sense content of sweat water.

9. The system of claim 8, wherein the at least one sensor includes a chemical field effect transistor (ChemFET).

* * * * *